United States Patent
Contijoch Mestres et al.

(10) Patent No.: US 7,087,769 B1
(45) Date of Patent: Aug. 8, 2006

(54) PROCESS FOR THE PREPARATION OF CATIONIC SURFACTANTS

(75) Inventors: Agustin Contijoch Mestres, deceased, late of Barcelona (ES); by Alex Contijoch Manent, legal representative, Barcelona (ES); by Monica Contijoch Manent, legal representative, Barcelona (ES); by Maria Contijoch Manent, legal representative, Barcelona (ES); Javier Rodriguez Martinez, Terrassa Barcelona (ES); Joan Seguer Bonaventura, Barcelona (ES)

(73) Assignee: Laboratorios Miret, S.A., Barcelona (ES)

( * ) Notice: Subject to any disclaimer, the term of this patent is extended or adjusted under 35 U.S.C. 154(b) by 64 days.

(21) Appl. No.: 10/467,780

(22) PCT Filed: Jun. 3, 2000

(86) PCT No.: PCT/EP00/05072

§ 371 (c)(1),
(2), (4) Date: Nov. 26, 2004

(87) PCT Pub. No.: WO01/94292

PCT Pub. Date: Dec. 13, 2001

(51) Int. Cl.
*C07C 231/00* (2006.01)
(52) U.S. Cl. .......................................... 554/69; 554/68

(58) Field of Classification Search ................ 554/168, 554/169
See application file for complete search history.

(56) References Cited

FOREIGN PATENT DOCUMENTS

EP    749960    * 12/1996

OTHER PUBLICATIONS

PCT International Search Report for subject application, issued Nov. 28, 2001 w/ following attachments: *J. Chem. Soc. Perkin Trans.* 1 1990 XP-000972986; and *Database Beilstein*, XP-002156958, vol. 41, No. 10, 1986.

* cited by examiner

*Primary Examiner*—Deborah D. Carr
(74) *Attorney, Agent, or Firm*—John W. Renner; Renner, Otto, Boisselle & Sklar

(57) ABSTRACT

The invention concerns the preparation of cationic surfactants derived from the condensation of an acid, preferably a fatty acid or a hydroxy acid with a number of carbon atoms of 8–14 with esterified amino acids, preferably basic-type amino acids, more preferably (L)-arginine. The method comprises a first step in which the esterifiction of the amino acid with an alcohol is performed and a second step for the condensation with a chloride of an acid, preferably an acyl chloride of a fatty acid or a hydroxy acid, whereby the second step is performed in an aqueous environment with a pH value between (6 and 7), preferably between (6, 7) and (6, 9).

9 Claims, No Drawings

PROCESS FOR THE PREPARATION OF CATIONIC SURFACTANTS

INTRODUCTION

The present invention relates to a new process for the preparation of cationic surfactant products, the hydrophilic portion of which consists of an esterified amino acid, preferably an esterified basic-type amino acid and the hydrophobic portion thereof consists of an acid, preferably a fatty acid or a hydroxy acid linked to the amino group of the amino acid via an amide bond.

BACKGROUND OF THE INVENTION

Cationic surfactant compounds are well-known in the art for their capacity to inhibit the formation of bacterial colonies.

This antimicrobial activity is described in detail in EP-A-0 749 960. The efficacy of the product lauramide of L-arginine ethyl ester monohydrochloride was proven against more microorganisms: *Escherichia coli, Staphylococcus aureus, Pseudomonas aeruginosa, Candida albicans* and *Aspergillus niger*. The product is further known to be efficaceous against the bacteria *Alcaligenes faecalis, Bordetella bronchiseptica, Citrobacter freundii, Enterobacter aerogenes, Klebsiella pneumoniae spp. pneumoniae, Proteus mirabilis, Salmonelly thyphimurium, Serratia marcescens, Bacillus subtilus, Bacillus cereus spp. mycoide, Micrococcus luteus, Arthrobacter oxydans, Mycobacterium phlei* and *Listeria monocytogenes*, against the yeasts *Rhodotorula rubra, Saccharomyces cerevisiae* and *Zygosaccharomyces rouxii* and and against the fungi *Mucor rouxii, Aureobasidium pullulans, Chaetonium globosum, Gliocadium virens, Penicillium chrysogenum* and *Penicillium funiculosum*. It is the particular advantage of the product, that it displays an excellent efficacy against these microorganism strains and is well tolerated by animals and human beings. This positive safety aspect makes the product highly suitable for any use leading to direct contact with the human body, like in cosmetic preparations and in the food industry.

The preparation of the cationic surfactant compounds with antimicrobial activity is described in the prior art.

The method described in ES-A-512643 is related to a first step of preparing an ester from the basic type amino acid and an alcohol and in the second step performing a condensation of the ester with a fatty acid to obtain the final product. It is a typical aspect of the method, that initially a solution of the catalyst thionyl chloride in the alcohol is prepared and that the amino acid is added to this solution. Heating of the solution is required and it takes at least 16 hours to bring the reaction to an end. The second step of the condensation is performed by adding the fatty acid as the free acid to the solution in the presence of a coupling reagent such as dicyclohexylcarbodiimide (DCDD).

An improved method has been provided in EP-A-0 749 960 which is differing from the previously mentioned method by providing in the first step a dispersion of the basic-type amino acid in alcohol and adding a catalyst like thionyl chloride to this dispersion in a drop-wise manner. It is the advantage of this adaptation of the method, that this drop-wise addition allows an excellent control of the reaction without the need of applying external heat to make the reaction run. A further difference is the performance of the second step by using a fatty acid halide. It is a particular advantage that this adaptation allows the performance of the reaction in an aqueous environment, which is a particular advantage, when the use of the final product is intended to be in the food industry. When the thionyl chloride is added, then arginine is solubilised for the formation of arginine ethyl ester dihydrochloride.

The method described in EP-A-0 749 960 is further characterised by the fact, that the second step of the condensation of the esterified amino acid is performed in an alkaline environment. EP-A-0 749 960 describes the need to perform the condensation at an alkaline pH, preferably at a pH between 8 and 10. The reason for using the alkaline environment is evidently the conviction in the art, that this type of reaction, which is a Schotten-Baumann reaction requires an alkaline environment. A comparable reaction is described in GB-A-1 352 420 which describes the reaction of arginine with a higher aliphatic acyl halide and likewise indicates the presence of an alkaline aqueous medium. A specific example contained in this prior art document indicates a pH value of 11.5–12.0 adjusted with sodium hydroxide.

The process described in EP-A-0 749 960 allows a relatively fast and efficient preparation of the wanted cationic surfactants to be used as antimicrobial products, but the inventors of the present invention have set themselves the task to continuously improve the preparative method in order to be able to produce the products industrially in the required quality in an economic manner. This continuous evaluation of improvements of the method has finally led to the present invention.

DESCRIPTION OF THE INVENTION

The present invention is directed to a novel method for the preparation of cationic surfactants suitable for antimicrobial use in cosmetics and food preparations. The inventive method can be used for the preparation of compounds prepared from any type of amino acid, preferred cationic surfactants prepared according to the inventive method are derived from basic-type amino acids, like (L)-lysine and (L)-arginine, particularly preferred is the amino acid (L)-arginine.

The amino acid, preferably the basic-type amino acid and even more preferably (L)-arginine is reacted in a first step of the inventive method with an alcohol to form the corresponding ester compound. The type of alcohol is not essential for the inventive method, but the preferred type of alcohol is an alcohol containing 1 to 12 carbon atoms whereby the alcohol can be linear or branched. Examples of such alcohols are methanol, ethanol, propanol, isopropanol, 1-butanol, 2-butanol, tert-butanol, pentanol, hexanol; heptanol, octanol, nonanol, decanol, undecanol and dodecanol. The preferred type of alcohol is ethanol, which is not only particularly suitable for the inventive method but is also preferable for the preparation of cationic surfactants to be used in the food industry while being well tolerated and being essentially free of toxic side effects.

The preferred way of preparing in the first step an ester from the amino acid and the alcohol in the inventive method corresponds to the method disclosed in EP-A-0 749 960. In this first step of the preparation a solution or dispersion of the amino acid in the alcohol is prepared and according to the preferred method a dispersion of the basic type amino acid in ethanol. The amino acids including the basic type amino acids are usually soluble in alcohols. However, the amino acid L-arginine monohydrochloride is not soluble in ethanol and for that reason a dispersion of this particular amino acid in ethanol is prepared to be the initial preparation of the inventive reaction.

To this solution or dispersion of the amino acid in the alcohol a suitable catalyst is added in a highly controlled manner. Any type of conventional catalyst can be used in this esterification step, like catalysts sulphuryl chloride, hydrogen chloride, phosphorus trichloride and phosphorus pentachloride, but the compound thionyl chloride has turned out to be particularly suitable as a catalyst. The catalyst, for instance thionyl chloride is added over a total period of two hours.

The total amount of the catalyst depends on the specific conditions of the reaction. In the method described in EP-A-0 749 960 it has been stated, that a total amount of 1.3 equivalents thionyl chloride is added to 1 equivalent of dispersed (L)-arginine, it has now been found out, that the highly specific amount of 1.27 equivalent of thionyl chloride leads to an optimum preparation of the ester, when the ester is formed from arginine with ethanol. The reason why this specific relative amount leads to the optimum final result is not clear at the present time. It has turned out, that in the industrial environment the catalyst thionyl chloride is added at a rate of 140 kg/h to 164 kg/h to obtain a final amount of the L-arginine ethyl ester dihydrochloride of 2100 kg of the crude final product, the purity of this crude product usually being between 90 and 95 %.

The controlled addition of thionyl chloride leads to a regular heat generation in the exothermic reaction which makes it possible to perform the reaction without heating from an external heat source. In particular in industrial production this way of performing the method is of great economic advantage.

The duration of the esterification reaction depends on a number of circumstances, in particular on the compounds used as constituents for the preparation of the ester. The conditions of the method for this part of the preparation allow a very fast preparation of the ester, a duration of 3 to 6 hours to finish the reaction is usual.

After the completion of the esterification reaction a final product is obtained which is usually a hydrochloride, in the case of the basic type amino acids usually a dihydrochloride. The product is crude, containing a number of further constituents such as a certain amount of the unreacted amino acid. The presence of such impurities is of no particular concern, purification can be performed but is certainly not necessary. Furthermore the yield of this esterification reaction is very good, in case of preparing the ester from the amino acid arginine and ethanol the yield is usually much higher than 90%, specific yields of 96% being regularly observed.

The product of the first step of the preparation, in more or less purified form, is obtained as an oily product. The solvent used in the esterification reaction of the invention is the alcohol, which solvent is removed carefully in order to avoid any unwanted effects during the second step of the reaction. Any kind of conventional method for the removal of the solvent is suitable, none is particularly preferred. The most regularly used method is the evaporation of the solvent under reduced pressure, under laboratory as well as industrial conditions. The purity of the product obtained in the first step is usually between 90 and 95% of the compound arginine ethyl ester dihydrochloride.

In the second step of the inventive method the esterified compound is further reacted with a carboxylic acid chloride to obtain the corresponding amide of the esterified amino acid. Basically any kind of acid chloride can be used in the inventive method, but fatty acid chlorides or hydroxy acid chlorides with a total number of carbon atoms between 8 and 14 are preferred and even more preferred linear chain fatty acid chlorides and hydroxy acid chlorides with a total number of 8 to 14 carbon atoms. Examples of such fatty acids are lauric acid, caprylic acid, caprylic acid, myristic acid and palmitic acid. Particularly preferred is lauroyl chloride, not only for the excellent performance in the reaction, but also for its excellent toxicological history.

It is one of the characteristics of the inventive method that this second step of the reaction is performed in an aqueous environment without the presence of any organic solvent. There are numerous possible uses of the final product, for which the presence of a minor amount of an organic solvent is of no particular concern, but as has been mentioned above repeatedly one of the specific intended uses of the products prepared according to the inventive method are in the food industry and any presence of organic components is unwanted under all circumstances. The preparation of the aqueous solution can be performed by stirring the ester of the amino acid in a suitable amount of water. As such water normal demineralised water, deionised water and destined water may be used, preferred is the use of deionised water.

It is one of the specific effects of the inventive method, that the pH value during the second step of the reaction is not kept in the alkaline pH range as was the case in the conventional way of preparing the product, but rather in a practically neutral pH range of 6.7–6.9. Numerous investigations have been performed by the inventors of the present invention during which it turned out, that in particular at this pH range the optimum values of the reaction yield are observed. A reaction yield of more than 90% can easily be obtained under these conditions which is a significant improvement over the yield obtained under the conventional reaction conditions. It is a further logical aspect of the inventive method, that the amount of impurities detected under these conditions is lower than under the conventional reaction conditions.

The dissolution of the reaction product obtained in the first step of the reaction leads to an aqueous solution of acidic character. According to the inventive process it is required to bring this pH value to a final value of 6.7–6.9 as the optimum pH range to perform the condensation reaction. This adjustment of the pH value can be performed with any basic product, as solution or alternatively by adding a dry basic compound. Addition of a solution is the most simple method and easiest to handle to obtain a precise and exact pH value under industrial conditions.

The type of basic product used to bring the pH value into the preferred range is of no particular importance, any kind of basic product may be used. In usual practice, the use of alkali metal hydroxides like sodium or potassium hydroxide is preferred, in particular of sodium hydroxide.

After adjusting the pH value to the wanted level, in particular to the pH level of between 6.7 and 6.9, the temperature of the reaction mixture is brought to a suitable level for the performance of the reaction. In the prior art the temperature was evidently not considered to be one of the key parameters since regularly the only indication found is the temperature to be below a level of 20° C., a more precise definition of the temperature apparently to be considered as of no particular concern. It is one further unexpected result obtained by the inventors of the present invention, that the temperature played a significant role in the determination of the final result of the reaction. A temperature between 10 and 15° C. turned out to be particularly suitable for the performance of the reaction, in particular since the obtained final amide turned out to display the highest purity of the obtained final amide. This optimum temperature of 10–15° C. is kept during the complete second step of the reaction.

The amidation reaction is started by the addition of the chloride of the fatty acid or of the hydroxy acid. The total amount of the chloride of the fatty acid or the hydroxy acid is 0.96 equivalent (per 1 equivalent of the esterified amino acid) instead of 1.1 equivalent as was indicated in the prior art.

The duration of the amidation reaction is 5 to 10 hours, a duration of 6 h is usual. When the condensation is performed, the final product is recovered by means of centrifugation of the precipitated product. On the conventional preparation method the pH had to be adjusted at the end of the preparation to a pH between 6 and 7, this additional adjusting step is now not required any more.

The final preparation of the product is performed with usual methods.

EXAMPLE

The method for the preparation of the cationic surfactant according to the invention displays a number of similarities with the method described in EP-A-0 749 960.

First Step

Preparation of L-arginine ethyl ester dihydrochloride.

In a glass reactor with a capacity of 2 liters with a five-socket lid and provided to with a mechanical stirrer, reflux condenser, nitrogen gas inlet, dropping funnel and thermometer, 1 equivalent of L-arginine hydrochloride is suspended in 200 ml of essentially water-free ethyl alcohol at room temperature and the stirring is started.

The catalyst thionyl chloride is added drop-wise in a total amount of 1.27 equivalents over a period of two hours, reflux conditions being maintained by additional heating. After the reaction mixture has reached the boiling point, stirring is continued for three further hours, after which the reaction is completed.

The solvent is removed by evaporation at reduced pressuer repeatedly, with intermediate additions of dry ethanol.

Second Step

Preparation of the lauramide of L-arginine ethyl ester monohydrochloride.

The crude reaction product obtained in the first step is dissolved in water and the pH of the solution is brought to a specific pH value by the addition of aqueous sodium hydroxide. The reaction conditions are investigated under conditions where the final pH of the reaction solution is between 4.5 and 12 (inclusive). The pH of the reaction is carefully kept constant at this value until completion of the reaction.

To the solution 0.96 equivalent of lauroyl chloride is added drop-wise, whereby the temperature of the mixture is kept at a temperature of 10–15° C. by means of an appropriate cooling bath containing ethylene glycol.

After completion of the reaction, the stirring is maintained for a further two hours, after which the pH of the solution is adjusted to a final value of 6–7 with hydrochloric acid or sodium hydroxide. Finally, the crude reaction product is filtered off, whereby a white solid composition of pearly appearance is obtained.

The obtained reaction product is analysed with standard chromatographic procedures in order to obtain the amount of the final product and the amounts and type of impurities present in the final product. The reaction yield was calculated.

The obtained data are displayed in the following table 1.

TABLE 1

| pH value | IMPURITIES | | | REACTION YIELD |
|---|---|---|---|---|
| | LAE (%, w/w) | LAS (%, w/w) | LAURIC ACID (%, w/w) | |
| 4.5 | 54 | 0.5 | 5.6 | 55–58 |
| 5.0 | 62 | 0.6 | 5.2 | 63–66 |
| 5.5 | 75 | 0.8 | 4.6 | 76–79 |
| 6.0 | 79 | 0.9 | 3.7 | 81–83 |
| 6.5 | 83 | 1 | 3.0 | 84–87 |
| 6.7–6.9 | 89 | 1 | 3.5 | 90–95 |
| 7.0 | 86 | 1 | 3.5 | 88–90 |
| 7.5 | 82 | 3 | 3.7 | 83–87 |
| 8.0 | 78 | 4 | 4.2 | 79–82 |
| 8.5 | 74 | 6 | 4.8 | 75–78 |
| 9.0 | 70 | 9 | 5.1 | 71–74 |
| 9.5 | 67 | 11 | 5.2 | 69–71 |
| 10.0 | 63 | 22 | 5.4 | 64–67 |
| 11 | 58 | 33 | 5.7 | 59–62 |
| 12 | 39 | 47 | 5.9 | 40–42 |

Explanation of abbreviations.
LAE ethyl ester of N$^\alpha$-lauroyl-L-arginine monohydrochloride
LAS N$^\alpha$-lauroyl-L-arginine
W/w weight/weight

The invention claimed is:

1. Method for the preparation of cationic surfactants derived form the condensation of an acid with an esterified amino acid comprising the esterification of the amino acid with an alcohol in a first step and in a second step performing the condensation with a chloride of an acid in an aqueous solution, characterised in that;
   the second step is performed at a pH value between 6 and 6.9.

2. Method according to claim 1, whereby the temperature in the second step of the method is kept at 10–15° C.

3. The method according to claim 1, wherein said amino acid is a basic-type amino acid.

4. A method according to claim 2, wherein said amino acid is a basic-type amino acid.

5. The method of claim 4, wherein said amino acid is (L)-arginine.

6. The method of claim 1, wherein said acid is a fatty acid or an hydroxy acid with a number of carbon atoms of 8–14.

7. A method according to claim 5, wherein said acid is a fatty acid or an hydroxy acid with a number of carbon atoms of 8–14.

8. A method according to claim 3, wherein said acid is a fatty acid or an hydroxy acid with a number of carbon atoms of 8–14.

9. The method of claim 1, whereby the pH value is between 6.7 and 6.9.

* * * * *